(12) United States Patent
Blomberg et al.

(10) Patent No.: US 7,322,937 B2
(45) Date of Patent: Jan. 29, 2008

(54) METHOD AND BREATHING APPARATUS FOR ASSESSING PULMONARY STRESS

(75) Inventors: Urban Blomberg, Solna (SE); Ake Larsson, Järfälla (SE); Kin-Chun Wong, Sundbyberg (SE)

(73) Assignee: Maquet Critical Care AB, Solna (SE)

( * ) Notice: Subject to any disclaimer, the term of this patent is extended or adjusted under 35 U.S.C. 154(b) by 812 days.

(21) Appl. No.: 10/706,812

(22) Filed: Nov. 12, 2003

(65) Prior Publication Data
US 2004/0097821 A1 May 20, 2004

(30) Foreign Application Priority Data
Nov. 20, 2002 (SE) .................................. 0203431

(51) Int. Cl.
*A61B 5/02* (2006.01)

(52) U.S. Cl. ..................... 600/538; 600/533; 600/538

(58) Field of Classification Search ..................... None
See application file for complete search history.

(56) References Cited

U.S. PATENT DOCUMENTS 5,316,009 A * 5/1994 Yamada ..................... 600/533
5,876,352 A * 3/1999 Weismann .................. 600/529
6,257,234 B1 7/2001 Sun
6,435,182 B1 8/2002 Lutchen et al.
2002/0110849 A1 8/2002 Leonhardt et al.

FOREIGN PATENT DOCUMENTS

EP 0 521 515 1/1993
EP 1 108 391 6/2001
WO WO 01/26721 4/2001

OTHER PUBLICATIONS

Patent Abstracts of Japan Publication No. 2000175886, for Japanese Application No. 10354751.

* cited by examiner

*Primary Examiner*—Robert L. Nasser, Jr.
(74) *Attorney, Agent, or Firm*—Schiff Hardin LLP

(57) ABSTRACT

In a method and breathing apparatus for assessing pulmonary stress, wherein pressure controlled flow of respiratory gas is generated, an ensuing flow is measured, resistance and compliance are determined based on measured pressure and flow and a stress index value is determined based on pressure, flow, resistance and compliance. The stress index value is 1 when no stress is present, $\geq 1$ when there is a risk for overdistension and $\leq 1$ when alveolar units are at a risk of being cyclically closed and opened. Implemented in a breathing apparatus the method can be used to assist an operator in diagnostic and therapeutic considerations in relation to a patient.

12 Claims, 2 Drawing Sheets

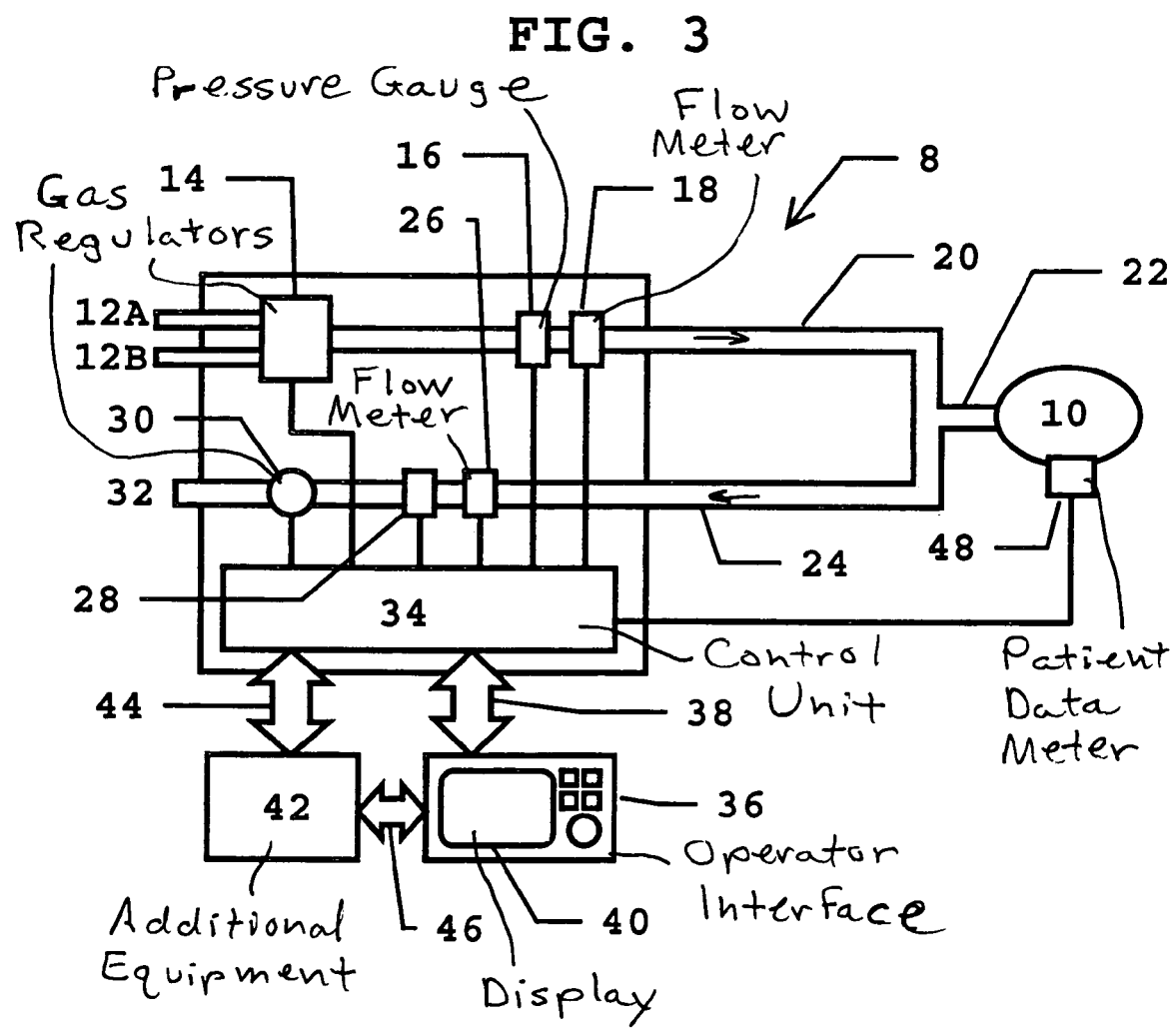

METHOD AND BREATHING APPARATUS FOR ASSESSING PULMONARY STRESS

BACKGROUND OF THE INVENTION

1. Field of the Invention

The present invention relates to a method for determining pulmonary stress as well as to a breathing apparatus operating according to the method

2. Description of the Prior Art

Mechanical ventilation is used as a life saving treatment in many circumstances, but it can also aggravate pre-existing disease and even induce lung injury if the dynamics and physiology of mechanical breath delivery are not considered. The lung has an inherent tendency to collapse. During normal breathing this tendency is counteracted by the chest wall and a natural substance called surfactant.

In disease the collapsing-tendency becomes more pronounced, giving rise to areas (alveolar units) collapsing early during exhalation/expiration and opening late during inhalation/inspiration. This cyclic opening and closing of airways may initiate lung injury manifested as gross air leaks, diffuse alveolar damage, pulmonary oedema and pulmonary inflammation, all of which have been termed Ventilator Induced Lung Injury (VILI). The cyclical opening and closing of alveolar units can be counteracted by the administration of a correctly set Positive End Expiratory Pressure (PEEP).

A second postulated mechanism for VILI is the delivery of large tidal volumes (which can cause volutrauma) or high end inspiratory airway pressure (which can cause barotrauma). Both may over-stretch lung tissues, leading to fluid accumulation, inflammation and increased stiffness of the lung. Baro-/volutrauma can be avoided by setting a proper tidal volume or peak pressure.

If the ventilator settings are not optimized, the period before VILI is manifest can be considered as a period of increased stress. Hence, a determination of the degree of lung stress that may follow from a specific ventilator setting can be considered as a pulmonary stress index (PSI).

In European Application 1 108 391, a method and apparatus addressing these problems is disclosed. The method described in this published application is based on P-t measurements made during constant flow inspiration.

SUMMARY OF THE INVENTION

An object of the present invention is to provide an alternative method for assessing the pulmonary stress.

The above object is achieved in accordance with the invention in a method that includes the step of obtaining measurements during inspiration with controlled gas pressure, but, in contrast to the method disclosed in European Application 1 108 391, there will be no P-t curve immediately obtainable through measured values (since pressure is controlled. Instead, an estimation is made by using mathematical formulas.

One advantageous analysis is to adopt a single compartment model for the lung. FIG. 1 shows this model using symbols equivalent to an electric circuit, having a resistance 2 in series with a compliance 4 (the compliance can be a variable dependent on volume). This provides the equation $$P(t) = R \cdot \dot{V} + \frac{1}{C(V)} \int_0^t \dot{V} dt + P(0) = R * \dot{V} + \frac{V(t)}{C} + P(0) \quad (1)$$

wherein P is airway pressure, V)(t) is lung volume, $\dot{V}$ is airway flow, R is resistance, C(V) is compliance and P(0) is the start pressure.

Compliance C(V) can be dependent on volume according to the equation $$C(V) = C \cdot V^{1-b} \quad (2)$$

wherein b represents the stress index and C is a constant.

Equations (1) and (2) can now be combined to a new equation $$P(t) = R \cdot \dot{V} + \frac{V^b}{C} + P(0) \quad (3)$$

Further, it can be assumed that the derivative of volume is equal to flow. Under the assumption that the flow is constant this leads to the following relationships $$\dot{V}(t) = Q \Rightarrow V(t) = Q \cdot t \quad (4)$$

wherein Q is flow.

Using (4) in equation (3) leads to $$P(t) = R \cdot Q + \frac{(Q \cdot t)^b}{C} + P(0) = R \cdot Q + \frac{Q^b}{C} \cdot t^b + P(0) \quad (5)$$

In European Application 1 108 391, the method was based on P-t measurements made during constant flow inspiration. In one embodiment of the method disclosed in this published application the following relationship was used assuming constant inspiratory flow:

$$P(t) = a + t^b \cdot c \quad (6)$$

wherein P represents airway pressure, t time, a and c are constants and b is the stress index. The value of b determines whether P(t) will be constant, concave or convex. These three basic shapes are shown in FIG. 2, where curve 6A is straight, curve 6B is convex and curve 6C concave. With a b varying over a breath sigmoidal relationships for P(t) is also possible. The convexity or concavity of P(t) was the indicator for stress (e.g. overdistension of lungs or cyclic closing and opening of lung compartments).

A comparison between equations (5) and (6) provides the following:

$$R \cdot Q = P(0) \quad (7)$$

$$b = b \quad (8)$$

$$c = \frac{Q^b}{C} \quad (9)$$

Based on measured flow and pressure the parameters R, b and 1/C can be determined from equation 5. Examples of methods for determining are least square method and iterative adaptation. This provides a value for b in a general case, which corresponds to the value for b in the specific case in equation (6).

Thus, if b≈1, compliance will be essentially constant, which corresponds to the healthy unstressed lung. If b is less than 1 the compliance is increasing during the inspiration (evident from equation (2)) and this implies risks associated with cyclic closing and opening of alveolar units. A value for b higher than 1 corresponds to a compliance decreasing during inspiration. This is associated with risks of progressive overdistension of the lungs.

Analysis can be performed on a breath-by-breath basis or on averaged values over a number of breaths.

It is of course possible to use other equations as starting point and arrive at the stress index value b in a similar manner. For instance, a two compartment lung model could be used.

Resistance in the airways can be calculated according the model $$R_{tot} = R_{lin} + \dot{V} \cdot R_{quad} \quad (10)$$

wherein $R_{lin}$ is a constant contribution and $R_{quad}$ is a flow dependent apparatus that operates according to the above-described method.

Basically, the apparatus includes a gas for regulating respiratory gas pressure (also providing values of pressure for the determination of stress index value), a flow meter for measuring a flow of gas towards the patient and a control unit for controlling the gas regulator. The control unit is adapted to perform the method described above.

More specifically, the control unit is adapted by hardware or software to carry out the determinations of R, C and b as related to equation (5) above.

In one preferred embodiment, the control unit compares the stress index value b with an interval, preferably with a lower limit between 0.5 and 0.95 and an upper limit between 1.05 and 1.5. As long as the stress index value b falls within the interval, there is no pulmonary stress. If the stress index value b thus provides both an indication of the presence of pulmonary stress and the magnitude thereof. The stress index value b therefore can be used as a value for pulmonary stress index, PSI.

Similar results are obtained when other mathematical expressions are used.

In another preferred embodiment, the apparatus also has a display unit and an alarm unit. The control unit is further adapted to perform at least one of a number of actions depending on, e.g., the value of the stress index value b (pulmonary stress index). It can generate an alarm when the stress index is too high or too low, indicating that a possibly injuries therapy is being delivered to a subject. It can display the stress index on the display unit. It can calculate suitable changes in control parameters for reducing pulmonary stress and display these as options for an operator on the display unit. It can automatically re-set the control parameters in accordance with calculations of suitable changes in the control parameters. It can determine if recruiting maneuvers should be provided. Hence, recommend/automatically perform recruiting maneuvers etc.

The apparatus according to the invention can advantageously be used for automatic re-setting of PEEP, tidal volume, airway pressure, I:E ratio or other ventilator-controlled parameters.

DESCRIPTION OF THE DRAWINGS

FIG. 3 is a block diagram of an embodiment of an apparatus according to the invention.

DESCRIPTION OF THE PREFERRED EMBODIMENTS

Figure 2:
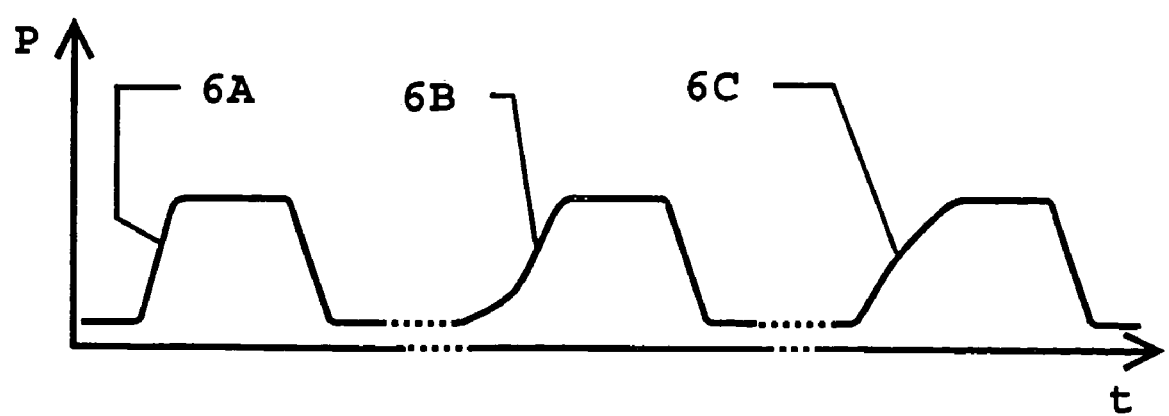
FIG. 2, as described above, shows three pressure-time curves illustrating the stress index.

In published European Application 1 108 391 the three different curves 6A, 6B and 6C shown in the pressure-time diagram P-t in FIG. 2 are discussed. The curves 6A, 6B and 6C are obtained by measuring the pressure during constant flow inspiration. The first curve 6A is essentially straight, the second curve 6B is convex and the third curve 6C is concave.

In the present invention and apparatus the same result is obtained by measuring flow during constant pressure inspiration. Pressure can be obtained through the control itself, but a separate pressure meter also can be used to obtain accurate pressure values in other parts of the apparatus or in the lungs of the patients.

The present invention is thus applicable for all situations where gas is supplied with a constant pressure or with a pre-set pressure profile (ascending, descending, triangular, sinusoidal, etc.). When using a pressure meter, the non-perfect obtained profiles can also be utilised for the determination. Supply is made is control mode, where a breathing apparatus exercises full control of supply.

According to the method of the present invention, the helpful information that can be obtained from the convexity or concavity of the P-t inspiration profile is essentially the same as described in the previously filed application, to which reference is hereby made for further details.

Figure 1:
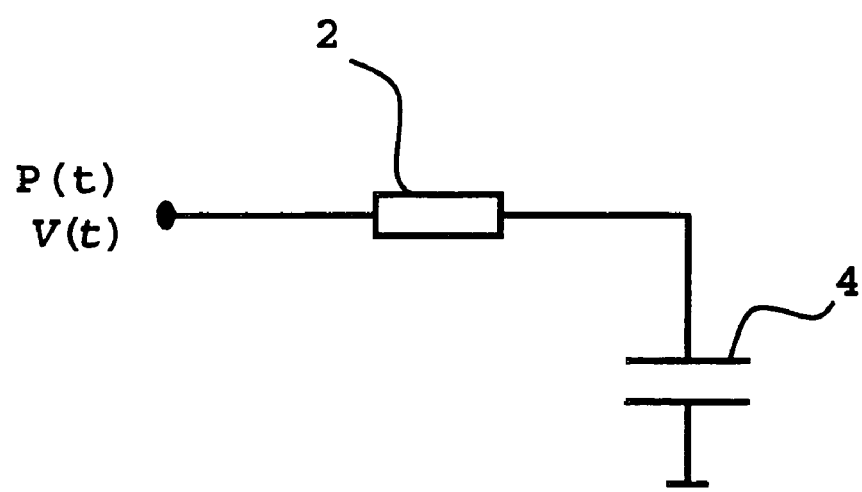
FIG. 1, as described above, shows a model for a single compartment lung.

One way of obtaining the stress index value b is to adopt measurements to a single compartment model of the lungs. This model is shown in FIG. 1. The lungs behave according to this model as a resistance 2 in series with a compliance 4. The compliance 4 can be dependent on volume.

The equations used to arrive at a relationship where a value for b can be arrived at by using flow, pressure, calculated resistance and compliance are shown above and need not be repeated here. Other equations can be used if a two compartment model or another model of the lung is used instead of the single compartment. The result is essentially the same.

Instead of mathematical models as the one above, other mathematical tools can be used to analyze the stress index value, such as artificial neural networks (ANN), pattern recognition systems, etc.

The following discussion reverts to the analysis described above, with b-values indicating one of the three curves of profiles.

The convex profile is an indication of a decrease in compliance with increasing tidal volumes. Such decrease during the inspiration is correlated to progressive overdistension. This basically means that the physical limit for expansion of the ventilated alveolar units has been reached. Treatment at this level may not only cause physical injury to lung tissue, but also may have detrimental effects on blood circulation through the lungs.

The concave profile is an indication of an increase in compliance with increasing lung volumes. Such increase is correlated to the opening up of alveolar units within the lungs. If a treatment were to display this kind of profile breath after breath (or as an average over a plurality of breaths), it is a sign of cyclic closing and opening of alveolar units. Such treatment is not ideal and may be injurious to the lungs.

In other works is it beneficial to the patient to arrive at a treatment where the straight profile predominates. This means situations where constant b is close to or equals 1.

Based on this, the constant b is used as an indication of the pulmonary stress. With b as a pulmonary stress index (PSI), the value of the stress index can be used to inform an operator of pulmonary stress. Since there are always variations in the real world, a normal or minimal stress index can be allowed to vary within a predefined interval. The interval could e.g. be 0.9-1.1. The interval can be set by an operator before starting a treatment.

Referring now to FIG. 3 which shows a breathing apparatus according to the invention. The breathing apparatus is generally indicated with numeral 8. The apparatus 8 can be connected to a subject, or patient 10. Essentially any animal with lung-dependent respiration can be contemplated as patient.

Gases can enter the apparatus 8 via a first gas inlet 12A and a second gas inlet 12B. The gas regulator 14 also regulates pressure and flow of the respiratory gas. The gas regulator 14 normally includes one or more valves for regulating down high-pressure gases, but in portable breathing apparatuses the regulator could also consist of a fan, compressor or similar device for generating a gas flow.

After the gas regulator 14, the respiratory gas passes a first pressure gauge 16 and a first flow meter 18. It then passes through an inspiration line 20 to a patient line 22 and into the patient 10.

From the patient 10 the respiratory gas will flow back through the patient line 22, into an expiration line 24 and via a second flow meter 26, a second pressure gauge 28 and a second gas regulator 30 to a respiratory gas outlet 32. The second gas regulator 30 is normally used to control respiratory gas flow during expiration for upholding a set end pressure (Positive End Expiratory Pressure—PEEP).

The pressure gauge 16, 28 and flow meters 18, 26 need not be located as shown. They can be built into, for instance, the gas regulators 14, 30. They can also be located elsewhere in the gas flow paths of the apparatus (such as inspiration line 20 and/or patient line 22 and/or expiration line 24). In particular is it possible to locate a pressure gauge within the patient 10 to measure lung or airway pressure. However, based on measurements from pressure gauges 16, 28 and flow meters 18, 26 as shown, corresponding values of e.g. airway pressure can be calculated in known manner.

The operation of the first gas regulator 14 and the second gas regulator 30 is controlled by a control unit 34. The control unit 34 also receives information from the pressure gauges 16, 28 and flow meters 18, 26. Based on the measured information the control unit 34 can comprise of any combination of known control components. It could for instance be micro processor based system including one or several processors and memories. Software programming could be used for carrying out the functions. It could also comprise, or include, hardwire components such as EPROM or similar. Other functions and tasks that the control unit 34 can perform are discussed below.

Via an operator interface 36 an operator of the apparatus 8 can communicated with, mainly, the control unit 34 via a first communication link 38. A display 40 can show programmed parameters, selectable functions and parameters as well as diagrams, suggested parameter, parameter waves, stress index and any conceivable information. The display 40 can consist of a CRT-screen, flat screen with or without touch sensitivity, plasma screen or any suitable screen for displaying images. The display 40 need not be integrated with the operator interface 36 and several displays can be used for one apparatus 8.

Additional equipment (e.g. further displays, PC, Intranet link to databases or remote monitoring stations, Internet link, etc.) is generally indicated with reference numeral 42. The operator interface 36 can communicate with the apparatus 8 via a communication link 38 to the control unit 34. The additional equipment 42 can communicate with the control unit 34 via a second communication link 44 and/or with the operator interface 36 via a third communication link 46. An externally connected PC could also form an integrated part of the control unit 34 for carrying out calculations.

Pressure controlled inspiration-related stress index can be determined during any pressure operation mode for the apparatus 8 where pressure is controlled. Pressure can be obtained through the control itself or measured with pressure gauge 16, 28, which, as mentioned above, can be positioned differently than indicated in the figure.

One example of how the apparatus 8 can be used for a patient 10 will now be described.

Suppose that a patient 10 having partially or completely collapsed lungs is connected to the apparatus 8. Although keeping the patient 10 alive is the primary goal, it should be done with minimum risk of causing further damage to the lungs. The control unit 34 therefore is programmed/constructed to perform a number of actions. These actions can be divided into phases, which can be carried out automatically or after initiative of an operator.

The first phase essentially includes life maintaining measures. The control unit 34 controls the first gas regulator 14 and second gas regulator 30 to provide respiration cycles having an initial tidal volume, an initial respiratory rate, an initial inspiratory time in relation the respiration cycle time, an initial oxygen fraction ($FiO_2$) and an initial PEEP value.

The initial values can be pre-programmed into the control unit 34, but preferably are entered either by the operator via the operator interface 36 or calculated by the control unit 34 based on patient data such as age, weight, diagnosis, or other available information regarding the status of the patient. $FiO_2$ could e.g. initially be set to 100%.

During the respiration cycles the control unit 34 also determines the stress index values on a regular basis and compares the stress index value with the predefined interval mentioned above. The interval can have a lower limit of ca. 0.6-0.95 and an upper limit of ca. 1.05-1.4, or any other interval reasonable in view of the patient's 10 initial condition. In the current example with a patient 10 with collapsed lungs, the stress index value will most likely fall below the predefined interval.

The second phase is basically meant to start to open up the lungs. The control unit 34 will then proceed by (mainly) controlling the second gas regulator 30 to achieve a progressive increase in PEEP. The increase will continue until the stress index value exceeds the lower limit, i.e. falls within the predefined interval. The increments by which PEEP is increased can be pre-programmed, calculated by the control unit 34 or entered by the operator.

In the third phase proper opening up of the lungs is the aim. To do this one or more recruiting manoeuvres are performed by the apparatus 8. A recruiting manoeuvre essentially consists of a prolonged inspiration (or rather inflation) at an elevated pressure in relation to the initial settings. The inspiration can last up to about a minute and the pressure can be up to 40-60 cmH$_2$O. Again, the values can be higher or lower depending on the specific circumstances at hand. Control parameters for the recruiting manoeuvre can be programmed, calculated by the control unit 34 or entered by the operator. Other recruiting manoeuvres can also be used.

After the recruiting maneuver(s) stress index value is again determined and compared with the predefined interval. Should the stress index be lower or even within the interval (but not optimal), the control unit 34 will control the second gas regulator 30 in increase PEEP again.

Another recruiting manoeuvre or manoeuvres is then supplied, followed by new determination of the stress index value.

This procedure of recruiting manoeuvre(s) and increase of PEEP value continues until the stress index value exceeds the upper limit of the predefined interval or the PEEP level exceeds a pre-set limit. This means that the lung has been fully recruited and can be regarded as fully open.

The fourth phase aims at reaching a proper setting for PEEP. The control unit 34 therefore controls the apparatus 8 to decrease PEEP, while determining the stress index value. When the stress index value falls within the interval, the settings regarding PEEP are essentially optimised.

Since the lungs are open, FiO$_2$ can be lowered. A proper decrease of FiO$_2$ is made when saturation of oxygen is decreased by 1-2%. A meter for saturation and, if required, other patient data is indicated with reference numeral 48 in FIG. 3. The decrease can be performed by the operator or by the control unit 34 (requiring access to saturation measurements).

When the operator wishes to select another ventilation mode, the control unit 34 can display the determined no stress setting on the display 40 as a suggestion to the operator.

Although modifications and changes may be suggested by those skilled in the art, it is the intention of the inventors to embody within the patent warranted hereon all changes and modifications as reasonably and properly come within the scope of their contribution to the art.

The invention claimed is:

1. A method for assessing pulmonary stress comprising the steps of:
    generating a pressure controlled flow of respiratory gas, at a pressure conforming to a constant pressure or pre-set pressure profile, associated with a subject having air waves exhibiting resistance and compliance;
    measuring said flow;
    determining said resistance and said compliance from said pressure and said low; and
    determining a stress index value, representative of pulmonary stress of said subject, from said pressure, said flow, said resistance and said compliance said stress index value having a magnitude that indicates whether the compliance is increasing or decreasing during inspiration.

2. A method as claimed in claim 1 comprising determining said stress index value from the relationship $$P(t) = R * \dot{V} + \frac{V^b}{C} + P(0)$$

wherein P(t) is airway pressure, V is lung volume, $\dot{V}$ is airway flow, R is resistance, C is a constant, and P(0) is a starting pressure.

3. A method as claimed in claim 1 comprising determining said stress index value on a breath-by-breath basis.

4. A method as claimed in claim 1 comprising determining said stress index value as an average over a plurality of breaths.

5. A breathing apparatus comprising:
    a respiratory line adapted for connection to airways of a subject, said airways exhibiting a resistance and a compliance;
    a regulator connected to said respiratory line that regulates a respiratory gas pressure to maintain said respiratory gas pressure at a pressure in said respiratory line conforming to a constant pressure or a pre-set pressure profile;
    a flow meter in fluid communication with said respiratory line that measures a flow of said respiratory gas in said respiratory line; and
    a control unit connected to said gas regulator to control said gas regulator, and said control unit determining said resistance and said compliance from said pressure and said flow and determining a stress index value, representative of pulmonary stress of said subject, from said pressure, said flow, said resistance and said compliance said stress and a value having a magnitude indicating whether the compliance is increasing or decreasing during inspiration.

6. A breathing apparatus as claimed in claim 5 wherein said control unit determines said stress index value according to the relationship $$P(t) = R * \dot{V} + \frac{V^b}{C} + P(0)$$

wherein P(t) is airway pressure, V is lung volume, $\dot{V}$ is airway flow, R is resistance, C is constant, and P(0) is a starting pressure.

7. A breathing apparatus as claimed in claim 5 wherein said control unit determines said stress index value on a breath-by-breath basis.

8. A breathing apparatus as claimed in claim 5 wherein said control unit determines said stress index value as an average over a plurality of breaths of said subject.

9. A breathing apparatus as claimed in claim 8 wherein said control unit employs a control parameter, as said at least one control parameter, selected from the group consisting of Positive and Expiratory Pressure, fraction of oxygen in the respiratory gas, and tidal volume.

10. A breathing apparatus as claimed in claim 5 wherein said control unit compares said stress index value to a predetermined interval and assesses said subject as exhibiting a minimum of pulmonary stress is within said predetermined interval, and assesses said subject as exhibiting pulmonary stress de to alveolar opening and closing if said stress index value is below said predetermined interval, and assesses said subject as exhibiting pulmonary stress due to alveolar overdistention if said stress index value is above said predetermined interval.

11. A breathing apparatus as claimed in claim 10 wherein said control unit employs an interval as said predetermined interval having a lower limit between 0.5 and 0.95 and an upper limit between 1.05 and 1.5.

12. A breathing apparatus as claimed in claim 5 comprising a display unit connected to said control unit for displaying humanly perceptible information, and an alarm unit connected to said control unit for emitting a humanly perceptible alarm, and wherein said control unit sets at least one control parameter for controlling breathing of the subject via said respiratory line, and wherein said control unit, dependent on said stress index value, takes at least one action selected from the group of actions consisting of generating an alarm via said alarm unit that pulmonary stress is present, generating a warning on said display unit that pulmonary stress is present, determining a change in said at least one control parameter and displaying said change on said display unit, determining a change of said at least one control parameter and automatically resetting said at least one control parameter according to said change, displaying a recommendation for a recruiting maneuver on said display unit, and automatically performing a recruiting maneuver.

* * * * *

UNITED STATES PATENT AND TRADEMARK OFFICE
CERTIFICATE OF CORRECTION

PATENT NO. : 7,322,937 B2
APPLICATION NO. : 10/706812
DATED : January 29, 2008
INVENTOR(S) : Urban Blomberg et al.

It is certified that error appears in the above-identified patent and that said Letters Patent is hereby corrected as shown below:

In column 3, cancel lines 26 and 27 and substitute the following therefor:
--contribution.
The above object also is achieved in accordance with the breathing apparatus that operates according to the above-described method.--

In column 5, line 24, after "a second gas inlet 12B." insert: --The gases are then mixed into a selected respiratory gas in a first regulator 14. One gas inlet would be sufficient if the respiratory gas was mixed outside the apparatus. More gas inlets can be used where the respiratory gas is to consist of more than two gases. In this embodiment air and oxygen are used as gases.--

In claim 5 at column 8, line 25, cancel "and a" and substitute --index-- therefor.

Signed and Sealed this

Fifteenth Day of July, 2008

JON W. DUDAS
*Director of the United States Patent and Trademark Office*